(12) United States Patent
Bysouth (10) Patent No.: US 7,448,566 B2
(45) Date of Patent: Nov. 11, 2008

(54) HIGH THROUGHPUT COMMINUTION/MIXING METHOD AND APPARATUS

(76) Inventor: Stephen Robert Bysouth, L'Auvrairie, Varenguebec, SRB (FR) 50250

( * ) Notice: Subject to any disclaimer, the term of this patent is extended or adjusted under 35 U.S.C. 154(b) by 23 days.

(21) Appl. No.: 11/350,880

(22) Filed: Feb. 10, 2006

(65) Prior Publication Data

US 2006/0175443 A1      Aug. 10, 2006

Related U.S. Application Data

(60) Provisional application No. 60/651,225, filed on Feb. 10, 2005.

(51) Int. Cl.
*B02C 17/08* (2006.01)
*B01F 11/00* (2006.01)

(52) U.S. Cl. .................. 241/175; 241/301; 366/217

(58) Field of Classification Search .............. 241/23, 241/30, 301, 175; 366/217, 235
See application file for complete search history.

(56) References Cited

U.S. PATENT DOCUMENTS

| | | | | |
|---|---|---|---|---|
| 2,216,089 A * | 9/1940 | Newton | .................... | 366/217 |
| 3,199,775 A * | 8/1965 | Drucker | .................... | 494/19 |
| 4,172,339 A * | 10/1979 | Balz | .................... | 451/329 |
| 4,638,600 A | 1/1987 | Kobayashi et al. | | |
| 4,718,199 A * | 1/1988 | Harper, Jr. | .................... | 451/329 |
| 5,375,783 A | 12/1994 | Gamblin | | |
| 5,551,779 A * | 9/1996 | Gantner et al. | .................... | 366/217 |
| 6,126,097 A | 10/2000 | Chen et al. | | |
| 6,749,332 B2 * | 6/2004 | Murakami | .................... | 366/217 |

* cited by examiner

*Primary Examiner*—Faye Francis
(74) *Attorney, Agent, or Firm*—Miles & Stockbridge P.C.; Gianna Julian-Arnold (57) ABSTRACT

The invention is a laboratory mill that allows small samples to be shaken, mixed, ground, homogenized or comminuted effectively within a small vial. The design is similar to a planetary mill but unlike those devices, neither axis of rotation is centered on the axis of the processing vessel. The design allows many vials to be processed at one time and even when the diameter of the vial is quite small, maintains the processing performance. The performance of the device when used as a comminuter is demonstrated showing that the device can comminute organic solids down to a median particle size of 1 micrometer with a narrow size distribution. Because the processing takes place within a vial, the mill does not require cleaning between samples which allows the application of the device in automated or high throughput systems. Since the action occurs in one plane, vials are able to be retained by a stationary plate above the vials and additionally makes the device amenable to automation of sample loading and unloading.

10 Claims, 8 Drawing Sheets

HIGH THROUGHPUT COMMINUTION/MIXING METHOD AND APPARATUS

RELATED APPLICATION

This patent application claims priority to U.S. Provisional Application Ser. No. 60/651,225 filed Feb. 10, 2005, which is incorporated herein by reference in its entirety.

FIELD OF THE INVENTION

This invention relates generally to means to mill, grind, comminute, mix or homogenize materials. More specifically, it is a sample processing instrument that can process many samples contained within vials at one time, without the need for cleaning. The design also allows automated loading and unloading of the processing instrument with samples using, for example, a robotic arm.

BACKGROUND OF THE INVENTION

A need was identified that required many samples to be comminuted (the grinding of a solid in the presence of a liquid) in an automated high throughput laboratory system. The constraints that this presented included: the ability to load and unload the device with vials using a robot; comminution at the desired scale of 5 to 40 ml; minimal or no clean-up of the system between samples; a mill that could hold more than 10 vials for parallel processing; comminution performance such that a particle size of 1 micron median distribution was obtained within less than 1 hour.

Laboratory milling and comminution systems that are generally available include conventional re-circulating mills, which can only process one sample at a time and need considerable clean up, shaker mills which require vials or well-plates to be clamped into the system and are therefore not 'robot-friendly', and planetary ball mills which also require the milling vessels to be clamped into the system, generally operate upon large vessels in the 80 ml to 250 ml range and use vessels that require sample clean-up. If smaller vessels are accommodated in the planetary mills, reducing adapters are used which allow the smaller vessels to be placed centrally in the location of the larger vessel.

SUMMARY OF THE INVENTION

The invention comprises a new type of planetary mill that can be used for the laboratory wet-milling, mixing and/or homogenization of materials at low volume scale. It allows many conventional laboratory vials to be placed in the mill at the periphery of vial holders, which are mounted where the normal grinding vessels are located in a conventional planetary mill. The resulting motion of the vials is best described as 'lunar' rather than 'planetary' rotation since they rotate about an axis that is not centered at the axis of the vial or may even be outside their centers, precisely like the moon rotates about the earth. In addition, they also rotate about a second axis precisely as the moon rotates with the earth around the sun. All this motion occurs in a single plane and the forces applied by the system only act within that plane. This operation in a single plane allows the vials to be placed in the system using, for example, a robot arm and, since the mass of these vials is low, held simply in place. Grinding action is provided by first loading the vials with small, dense beads such as of glass, metal or ceramic of for example diameters between 0.5 and 5 mm, along with the materials to be processed. The vials are then closed, placed in the mill and the motion started. After the designated processing time, the motion is stopped and the complete vial and contents removed leaving the mill clean and ready to receive another vial.

Where desired, this system can therefore be continuously loaded and unloaded with samples and thence process hundreds of samples per day. Similarly this throughput can be further enhanced through the use of automation. No mill cleaning is required and the processed materials can be removed from the vials elsewhere and the vial cleaned or disposed of.

It is an object of the present invention to provide a means to alternatively or concurrently, mill, comminute, mix, grind or homogenize samples in the range of, but not limited to, 5 to 40 ml.

It is a further object of the present invention to enable conventional glass laboratory vials to be used to contain the materials to be processed.

It is a further object of the present invention to enable samples to be loaded into the present invention using robotic devices.

It is a further object of the present invention to provide such a system without the requirement of cleaning, so that fresh samples may be loaded and processed immediately after unloading of the previous batch of vials.

It is a further object of the present invention to provide such a system for the processing of samples in laboratories.

It is a further object of the present invention to provide the means to either process vials independently or in batches of multiple vials simultaneously.

There has thus been outlined, rather broadly, the more important features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced or carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that equivalent constructions insofar as they do not depart from the spirit and scope of the present invention, are included in the present invention.

For a better understanding of the invention, its operating advantages and the specific objects attained by its uses, reference should be had to the accompanying drawings and descriptive matter, which illustrate preferred embodiments of the invention.

DETAILED DESCRIPTION OF THE INVENTION

A system is disclosed herein for the milling, mixing and/or homogenization of laboratory samples. Further, the disclosed, illustrative embodiments can be used, for example, with vials from 5 to 80 mL, filled to about 25% with test formulation. The use of a 40 ml vial is demonstrated as one embodiment. The embodiments disclosed herein are disclosed for illustrative purposes only, alternative embodiments are envisioned.

Figure 1:
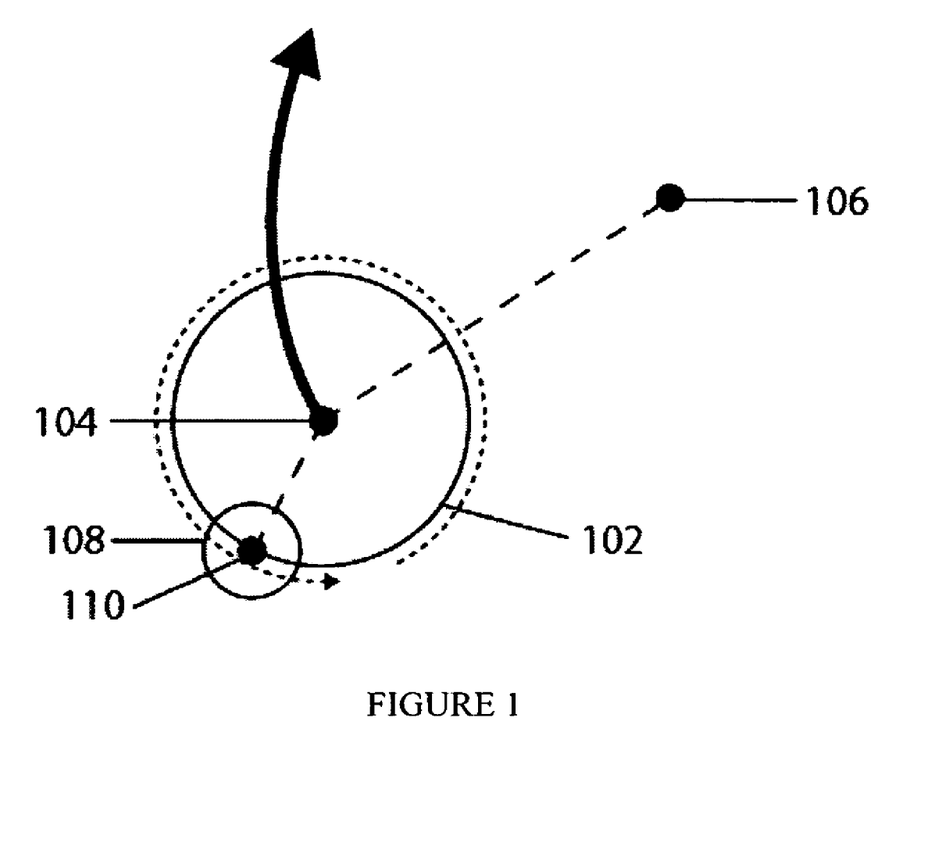
FIG. 1 illustrates the motion of vials in the mill shown from above.

FIG. 1 illustrates how the motion of the vials differs in the illustrated embodiment of the present invention from the motion of vessels in a conventional planetary ball mill. In a conventional planetary mill, large vessel 102 being used for processing is located and centered at location 104 and rotates about its own axes, also at location 104. This rotating vessel is then caused to counter-rotate around a second principal axis 106. However, in the preferred first embodiment, vial(s) 108 is at second location 110 and experiences a first degree of rotation about an axis that is not coincident with the vial axis and as in the illustration, can be outside its volume at location 104. It also is caused to counter-rotate around a second axis 106. In the preferred first embodiment, the speed of rotation about the smaller radius centered on location 104 is twice that of the speed of rotation of the larger radius centered second axis 106.

Figure 2:
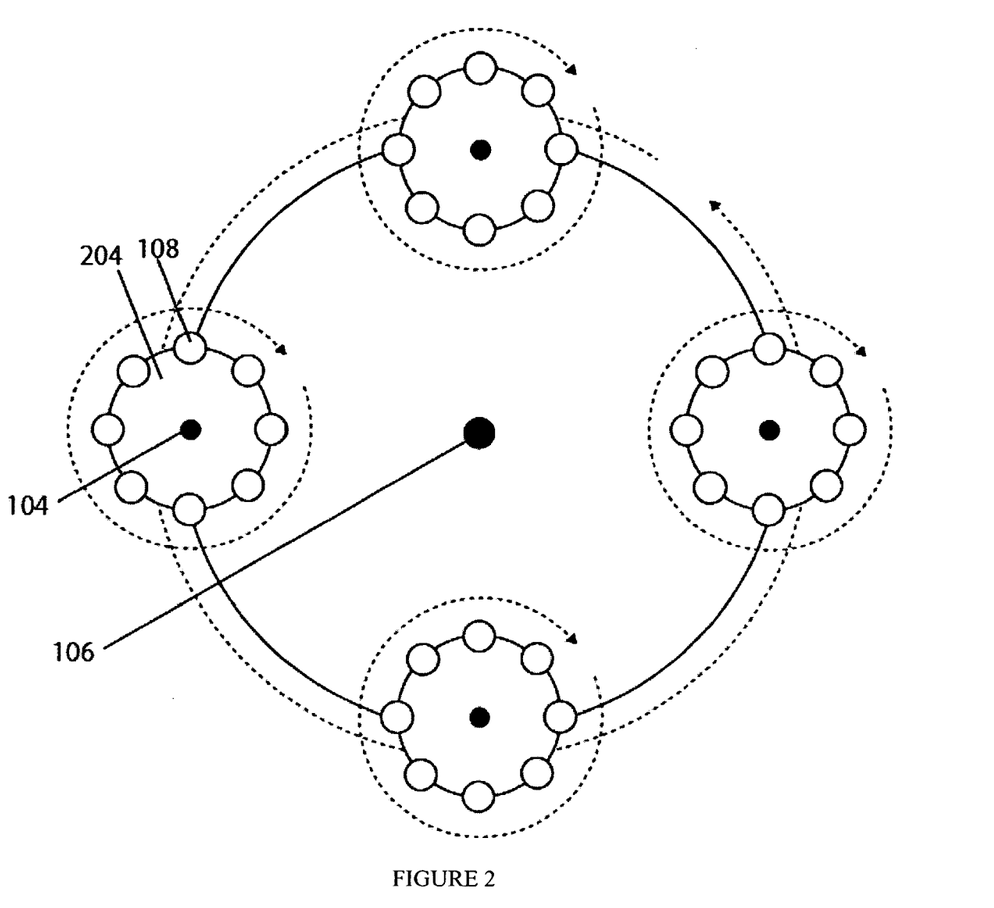
FIG. 2 illustrates the placement of multiple vials in the system, shown from above.

FIG. 2 illustrates how vial(s) 108 can be arranged in the preferred first embodiment so that they experience identical motion. In the preferred first embodiment as illustrated here, vial holder(s) 204 are arranged each to hold 8 vial(s) 108 allowing up to a total of 32 vials to be processed at one time in this embodiment. In addition, by making the ratio of rotation a whole number and stopping the motion when the vial holder reaches the position illustrated, the preferred first embodiment presents the robot with a predicable location to retrieve or place the vials. Again, the principle axis of rotation 104 and the secondary axis 106 are shown.

Figure 3:
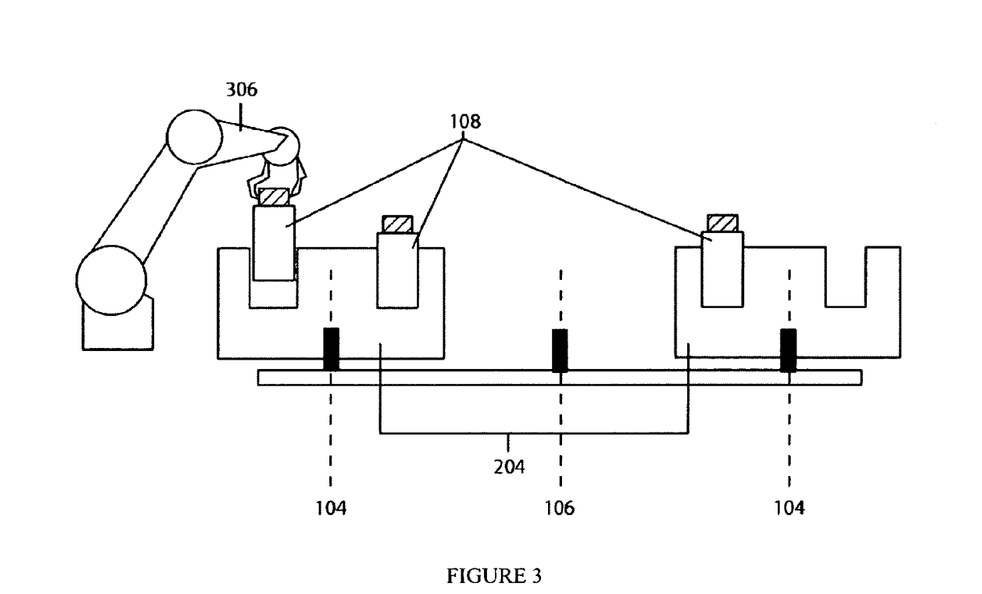
FIG. 3 illustrates the vial placement shown from the side and how a robot arm may access the system.

FIG. 3 illustrates as a cross section of the device, how the vials 108 can be contained within the preferred first embodiment using vial holders 204 and accessed by robotic arm 306. Also shown are the two axes of rotation, axis 104 and axis 106.

Figure 4:
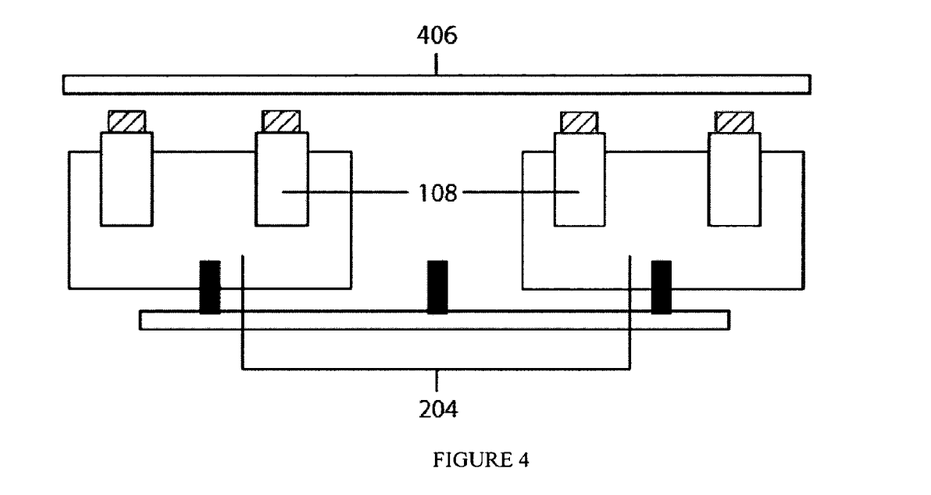
FIG. 4 illustrates vial retention using a retention plate

FIG. 4 illustrates how in the preferred first embodiment, vial(s) 108 can be held within vial holder(s) 204 when rotating, by stationary retention plate 406.

Figure 5:
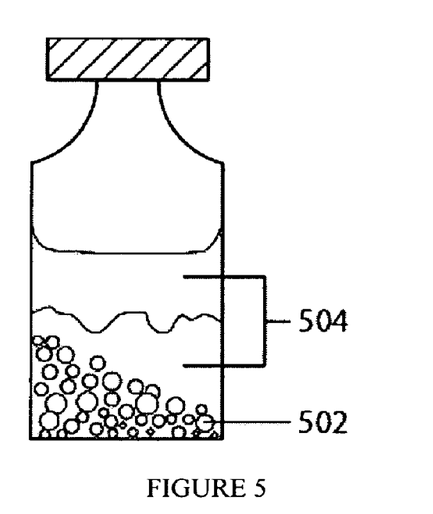
FIG. 5 illustrates a closed vial containing grinding beads and materials to be processed.

FIG. 5 illustrates the closed vial used in the preferred first embodiment containing beads 502 and materials to be processed 504. Materials to be processed 504 can be liquids, solids or mixtures.

Before constructing the preferred first embodiment described, a mathematical model was constructed to try to determine the effect of moving both axes of rotation such that neither is coincident with the processing vial or jar axis and the effect of using small vials to contain the material to be processed. The model showed that the forces exerted on the material to be processed depended on the speed of rotation about the principal axes of rotation, the ratio of the two rotation speeds, the radii of rotations about the two axes, and the diameter of the vial used for processing.

Figure 6:
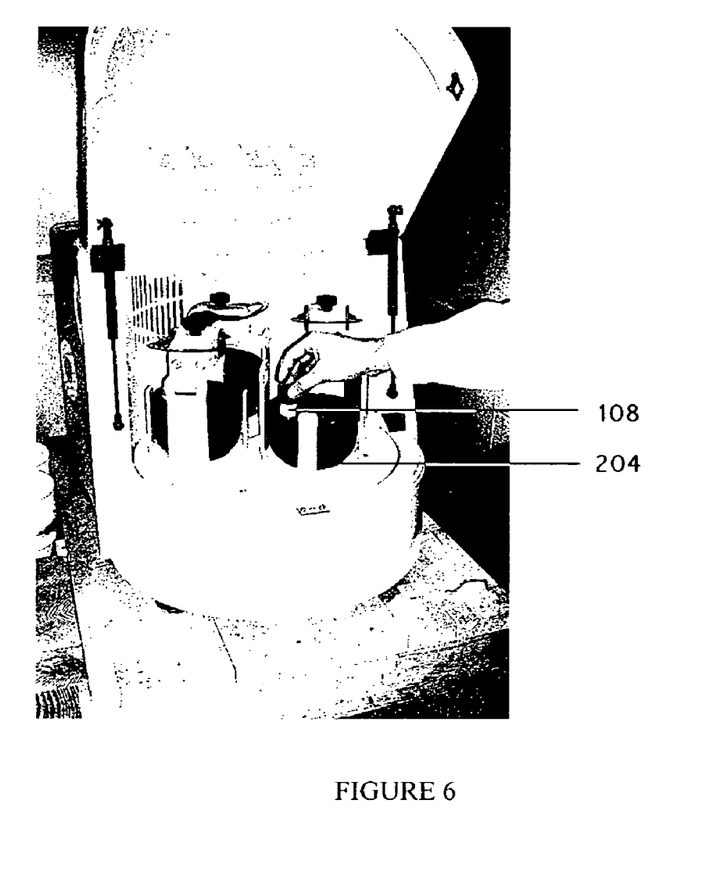
FIG. 6 shows one of the preferred embodiments of the invention containing vials to be processed and showing vial placement.

FIG. 6 shows a second embodiment that allow vial(s) 108 to be placed in the same location as in the preferred first embodiment but is based on a commercially available planetary mill where the conventional jars of a commercial planetary mill have been replaced by vial holders 204 in the same format as in the preferred first embodiment but requiring a lid to be clamped in place to prevent movement of the vial holder and vials therein. In addition to these changes, the ratio of the relative rotation speeds about the two axes of rotation was changed from that normally supplied of 1:2.19 to the ratio specified in the preferred first embodiment of 1:2.

This second embodiment FIG. 6, was used in a program of experiments to determine whether the new format of the invention in the preferred first embodiment illustrated in FIG. 1, would perform comminution of organic materials and meet the objects of the invention in terms of performance and examine some variables.

Experimental Program

The experiments carried out using the second embodiment investigated the parameters of volume of material to be processed in the small vial, the ingredients of the material to be processed, the ratio of beads to the volume of the processed material and the order of addition of the beads and material to be processed.

Additional preliminary experiments also indicated that steel was not a preferred grinding material due to contamination of the sample with metal from the beads. So, in these experiments, alternative bead materials were tested including glass and zirconia.

After processing, the particle size distributions of the comminuted solids were compared with one another, and with samples milled by classical milling, classical milling being known by one of ordinary skill in the art. The particle size distributions were measured using a Malvern Mastersizer. Similarly, comparisons were also made to distributions using the conventional planetary mill with larger jars.

The following solid ingredients were used with the intent to produce suspensions and before processing, consisted of particles in the size range 80 to 200 μm:

Ingredient A: $N^2$-tert-butyl-6-chloro $N^4$-ethyl-1,3,5-triazine-2,4-diamine, Melting point 177-179° C.;

Ingredient B: (EZ)-3-(2-chloro-1,3-thiazol-5-ylmethyl)-5-methyl-1,3,5-oxadiazinan-4-ylidene(nitro)amine, Melting point 139° C.; and Ingredient C: methyl(E)-2-{2-[6-(2-cyanophenoxy)pyrimidin-4-yloxy]phenyl}-3-methoxyacrylate, Melting point 114-116° C.

These ingredients were added to the vials in varying amounts as per the experiment, along with beads and the liquid phase materials (water, surfactants, dispersants and antifoams). The rotation speed of the mill was operated at 400 rpm, which was the speed about the second principal axis, 106, FIG. 1.

Experimental variables included fill volume in the vial, bead material and size, bead to sample ratio, time at speed, and fill order (in other words, which phase is dispensed first and when the balls are added). Additionally, the solid ingredient itself was varied as above. Despite the resulting large number of experiments, the ability to run 32 vials at the same time provided by this preferred embodiment, enabled and demonstrated the desirable high throughput and enabled rapid data gathering.

The experiments are summarised in Table 1.

TABLE 1

Experimental Summary for Studies Using the Invention for Comminution

Figure 7:
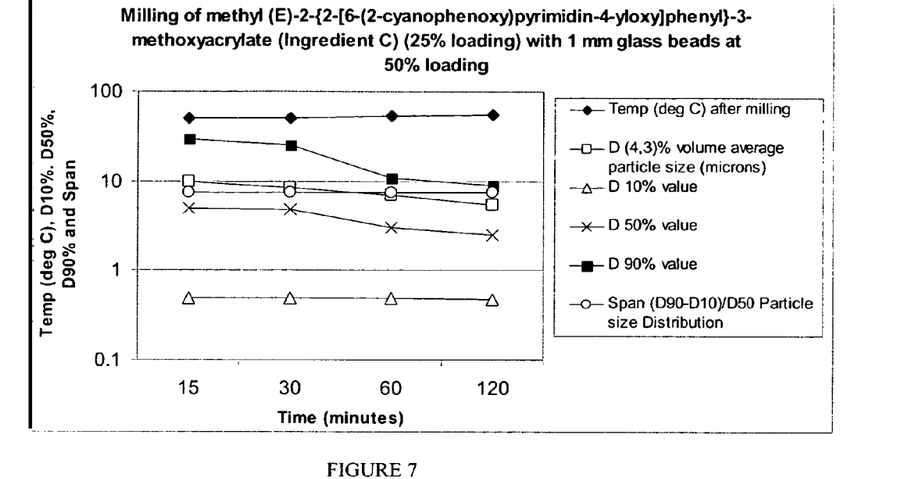
FIG. 7 shows how the particle size distributions decrease over time for glass beads at a 50% loading level.

| Parameter Varied | Parameter Values Used | Fixed Parameters & their values | Figure |
|---|---|---|---|
| Milling times (minutes) | 15, 30, 60, 120 | Each value used for all experiments | |
| Solid Ingredient | A, B and C | Used as defined | |
| Time only (minutes) | 15, 30, 60, 120 | Solid ingredient: C Formulation 25% active:75% liquid Relative bead loading 0.5 1 mm zirconia beads | FIG. 7 |
| Relative bead loading (bead volume per mass of solid) ml/g | 1.00, 0.75, 0.50 | 1 mm glass beads Solid ingredient: C Formulation- 25% solid:75% liquid | FIGS. 8 and 9 |
| Bead size (mm) | 1, 2 | Glass beads Solid ingredient: B Formulation- 25% solid:75% liquid Bead loading 1.0 | FIG. 10 |
| Bead size (mm) | 1, 2 | Glass beads Solid ingredient: B Formulation- 50% solid:50% liquid Bead loading 0.75 | FIG. 10 |
| Relative % solid loading: (mass of solid dispersed in the volume of liquid phase as %) g/100 ml | 25, 50 | 1 mm glass beads Solid ingredient: B Bead Loading 1.0 | FIG. 10 |
| Relative bead loading (bead volume per mass of solid) ml/g | 1.00, 0.50 | 1 mm glass beads Solid ingredient: B Formulation- 50% solid:50% liquid | FIG. 10 |
| Relative bead loading (bead volume per mass of solid) ml/g | 1.00, 0.75, 0.50 | 1 mm ceramic beads Solid ingredient: A Formulation 50% solid:50% liquid | FIG. 11 |
| Relative bead loading (bead volume per mass of solid) ml/g | 1.00, 0.75, 0.50 | 1 mm glass beads Solid ingredient: A Formulation 50% solid:50% liquid | FIG. 12 |
| Bead material (affecting their hardness an density) | glass, zirconia | Bead size 1 mm Solid ingredient: C Formulation- 25% Solid:75% liquid Relative bead loading 0.6 Full vial at ~25 ml total volume | FIG. 13 |

Discussion

These results demonstrate the usability of the mill as a comminution device for solid ingredients in a variety of formulations. It is apparent that milling between 30 and 60 minutes provided sufficient milling to obtain a narrow particle size distribution and a mean particle size below 1 micron. The experiments also clearly demonstrated that the preferred embodiment is suitable for use in High Throughput Experimentation. Calculations show that for recipes using the preferred embodiment as a comminuter, the sample capacity, robot accessibility and performance make these embodiments desirable and suitable for many applications.

Figure 8:
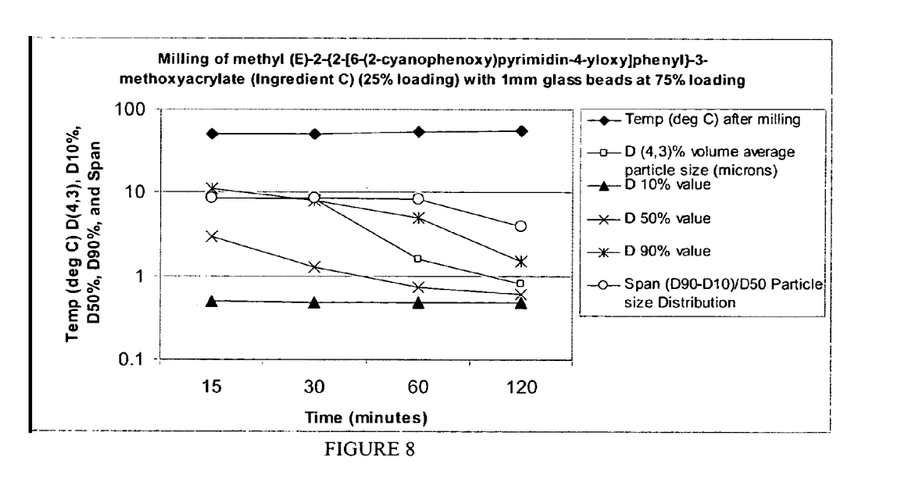
FIG. 8 shows how the particle size distributions decrease over time for glass beads at a 75% loading level.
Figure 9:
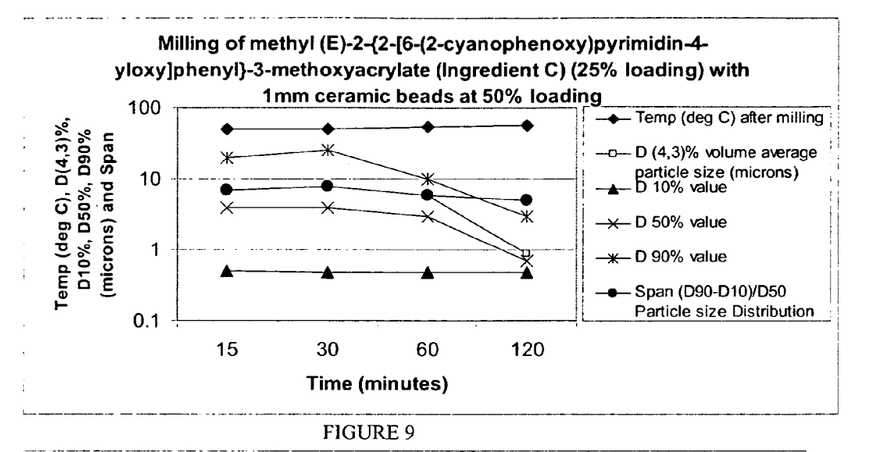
FIG. 9 shows how the particle size distributions decrease over time for zirconia beads at a 50% loading level.
Figure 10:
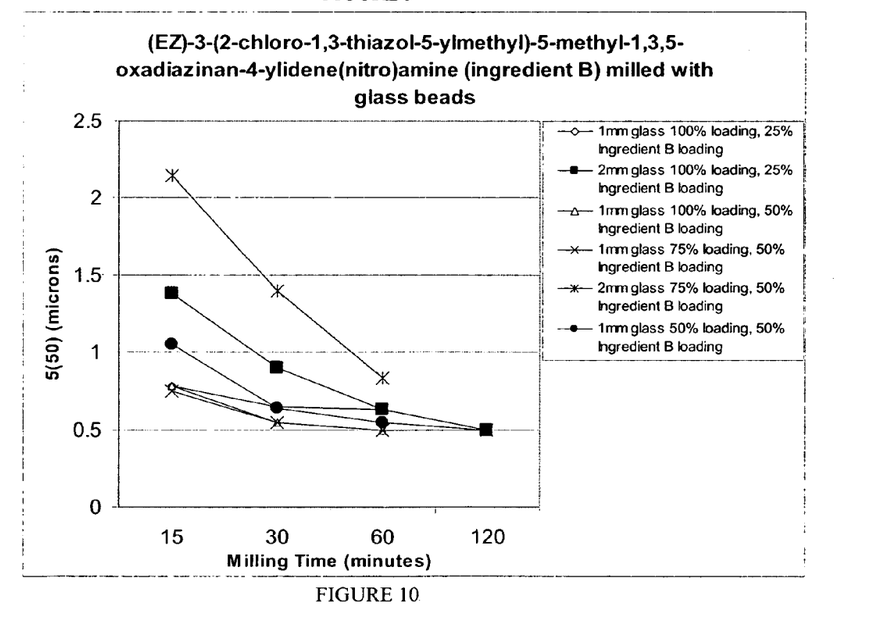
FIG. 10 shows the particle size reduction of (EZ)-3-(2-chloro-1,3-thiazol-5-ylmethyl)-5-methyl-1,3,5-oxadiazinan-4-ylidene(nitro)amine using various glass bead loading levels.

It should be noted that during milling, there was a marked increase in temperature as shown in FIGS. 8 and 9, which are plotted on log scales. In the second embodiment used in these experiments, the vial holders are constructed of Delrin polymer, which insulates the processed materials from heat loss. The commercial systems have a fan which blows air into the milling enclosure and, by designing the vial holders appropriately using such things as a more open arrangement, aluminium, incorporating cooling holes, etc., the effective heating is reduced in the first embodiment to tolerable levels. Additionally, by operating the mill intermittently as in the case where samples are added and removed during a long experiment, natural cooling occurs during these 'rest periods'.

For the solid ingredient B, higher bead loading correlated to more efficient milling. For two experiments with this formulation, it is apparent that higher solid loading also produces more efficient milling.

Figure 11:
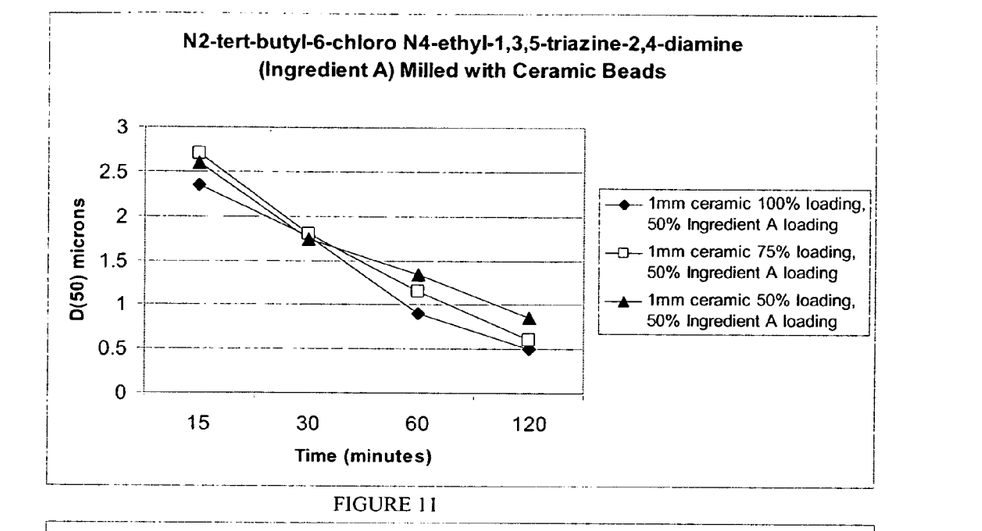
FIG. 11 shows the particle size reduction of $N^2$-tert-butyl-6-chloro $N^4$-ethyl-1,3,5-triazine-2,4-diamine using various zirconia bead loading levels.
Figure 12:
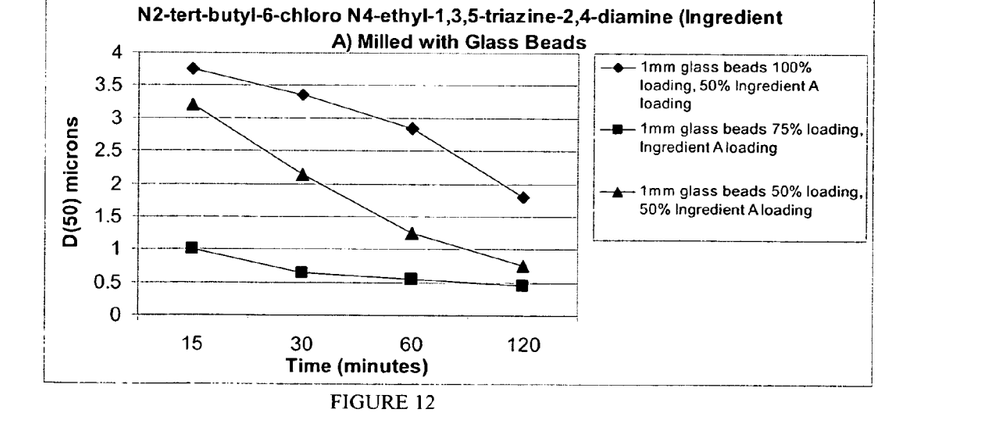
FIG. 12 shows the particle size reduction of $N^2$-tert-butyl-6-chloro $N^4$-ethyl-1,3,5-triazine-2,4-diamine using various glass bead loading levels.
Figure 13:
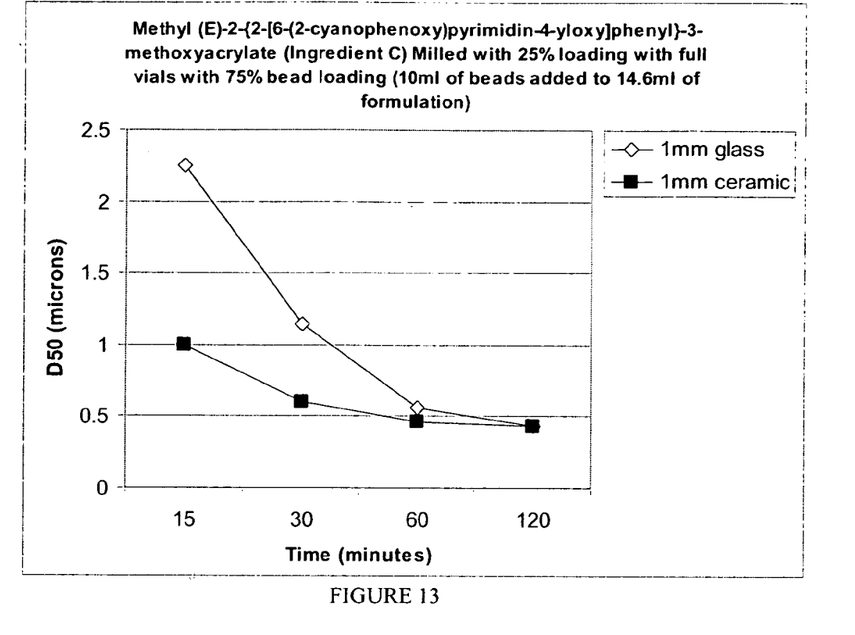
FIG. 13 shows the particle size reduction of a full vial containing $N^2$-tert-butyl-6-chloro $N^4$-ethyl-1,3,5-triazine-2,4-diamine using various glass bead loading levels.

The data shown in FIGS. 11 and 12 also demonstrates that using denser and harder beads (zirconia), produces a more consistent milling for ingredient A over the range of solid loading. These beads also mill to a finer particle size in a shorter time. The greater efficiency obtained with the zirconia beads is confirmed in FIG. 13 for ingredient C as the solid ingredient due to both the denser material and greater hardness.

Conclusion

The preferred embodiment used for these experiments which has the adjusted rotation ratio and radially arranged vials so that both axes of rotation are not coincident with the axis of the vials and in this case are both outside the vial, when used as a planetary comminuter, is able to grind the three solid ingredients defined herein to the desired particle size.

Having now described embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, since numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for processing materials comprising: a first location; a second location; and a third location, wherein each said first location, second, location and third location is not coincident with each of the other said locations and wherein a vessel is centered at said third location; at least one rotating means wherein said rotating means rotates said vessel around a first axis, said first axis having a first radius of rotation centered on said first location; and at least one additional rotating means wherein said additional rotating means rotates or counter-rotates said vessel around a second axis, said second axis having a second radius of rotation centered at said second location.

2. The device for processing materials of claim 1, wherein said rotating means rotates said vessel around said second axis, wherein said vessel has an axis and wherein said second axis is not coincident with said vessel axis.

3. The device for processing materials of claim 1, wherein said rotating means counter-rotates said vessel around said second axis, wherein said vessel has an axis and wherein said second axis is not coincident with said vessel axis.

4. The device for processing materials of claim 1, wherein said rotating means has an adjustable speed of rotation and wherein said additional rotating means has an adjustable speed of rotation.

5. The device for processing materials of claim 1, wherein said additional rotating means rotates about twice as fast as said rotating means.

6. The device for processing materials of claim 1, wherein at least one of said rotating means and said additional rotating means further comprises a means of controlling rotation speed.

7. The device for processing materials of claim 1, further comprising: a vessel(s) stability means, wherein said vessel(s) stability means stabilizes said vessel(s).

8. The device for processing materials of claim 7, wherein said vessel(s) stability means is a clamp, vial holder, or stationary retention plate.

9. The device for processing materials of claim 1, further comprising a heating means, wherein said heating means provides heating of materials within said vessel(s).

10. The device for processing materials of claim 1, further comprising a cooling means, wherein said cooling means provides cooling of materials within said vessel(s).

* * * * *